United States Patent [19]
Grover et al.

[11] Patent Number: 6,133,548
[45] Date of Patent: Oct. 17, 2000

[54] APPARATUS AND METHOD FOR HEATING MICROSCOPE SLIDES

[76] Inventors: Marilyn L. Grover, 123 W. Center St., Hyde Park, Utah 84318; Patti A. Nelson, 8343 S. Highway 165, Paradise, Utah 84328; Gary D. Bradshaw, 175 W. 700 South, Wellsville, Utah 84339; Barry O. Stokes, 130 W. 1260 South, Logan, Utah 84321; Dennis R. Briscoe, 149 E. 200 North, Providence, Utah 84332; Carmelo G. Quirante, 1225 Eastridge Dr., Logan, Utah 84321

[21] Appl. No.: 09/320,434

[22] Filed: May 26, 1999

[51] Int. Cl.$^7$ ........................................... F24C 7/10
[52] U.S. Cl. .......................... 219/386; 219/385; 219/521; 237/3; 236/3
[58] Field of Search ................... 219/385, 386, 219/394, 428, 521; 34/202; 237/3; 236/2, 3

[56] References Cited

U.S. PATENT DOCUMENTS

| | | |
|---|---|---|
| 3,701,201 | 10/1972 | Drury ......................................... 34/60 |
| 4,384,193 | 5/1983 | Kledzik et al. .......................... 219/521 |
| 5,276,310 | 1/1994 | Schmidt et al. ......................... 219/521 |
| 5,525,512 | 6/1996 | Pieler et al. .......................... 435/303.1 |
| 5,782,174 | 7/1998 | Cohn et al. ............................... 99/476 |

*Primary Examiner*—Teresa Walberg
*Assistant Examiner*—Shawntina T. Fuqua
*Attorney, Agent, or Firm*—Mallinckrodt & Mallinckrodt; Philip A. Mallinckrodt

[57] ABSTRACT

In accordance with the apparatus of the invention, a preferably vertically upstanding housing is provided, internally thereof, with a rack structure having an upstanding series of shelves, or other microscope-slide-supporting members, spaced one above another providing multiple, substantially horizontal slots arranged alternatively with the shelves and leading into corresponding compartments between the shelves for receiving microscope slides to be heated, which preferably lie flatwise on and against the shelves so as to be heated by conduction from the shelves.

The method of the invention constitutes the placing of the slides in the heating compartments, preferably with corresponding ends projecting therefrom so as to remain relatively cool for grasping during removal, and turning on the heat.

12 Claims, 8 Drawing Sheets

APPARATUS AND METHOD FOR HEATING MICROSCOPE SLIDES

BACKGROUND OF THE INVENTION

1. Field

This invention is concerned with the heating of microscope slides on which are usually mounted specimens to be examined, and relates to both heating apparatus and methods.

2. State of the Art

Some heaters for multiple microscope slides have been developed heretofore.

Thus, U.S. Pat. No. 3,701,201 granted on Oct. 31, 1972 to James H. Drury entitled "Microscope Slide Dryer" shows and describes a drying receptacle for a series of specimen-bearing, microscope slides, which have one set of ends inserted in a series of side-by-side receiving slots near the bottom of and at the front of the receptacle, so as to hold the series of elongate slides extending vertically upwardly and face-to-face past a heater lamp placed forwardly in the receptacle, a motor-driven fan being positioned in the back portion of the receptacle to force air across the heater lamp and between the series of slides before discharge at the front of the receptacle.

U.S. Pat. No. 4,384,193 granted on an invention of Gary S. Kledzik and Glenn A. Wilson on May 17, 1983 for an "Incubatory Device", presents the upper face of a tray-like structure to a user for the insertion of multiple microscope slides flatwise in and across an elongate, shallow, receiving recess arranged above a transverse series of slide-supporting and slide-heating blocks. Specimens carried by the slides are incubated by the supplied heat and by liquid reagents. Cleaning solution can be poured on the slides from the open top of the tray structure.

SUMMARY OF THE INVENTION

In accordance with the apparatus of the invention, an upstanding rack structure provides a series of microscope-slide-supporting members, one above another, each member extending transversely of the rack to form heating compartments between mutually adjacent members, each compartment adapted to receive at least and preferably only one microscope slide for heating. In accordance with the method of the invention, the microscope slides are placed in the heating compartments by the user preferably so that corresponding ends thereof protrude from such heating compartments so as to remain relatively cool and accessible for grasping manually to remove them from the apparatus.

Heating of the slides within the compartments is preferably accomplished by conduction of heat through the supporting members, which are preferably shelves extending from and formed integrally with an upstanding wall of the rack structure, and such rack structure is preferably positioned in an upstanding housing that opens into a series of slots leading into the heating compartments, respectively.

THE DRAWINGS

An embodiment of apparatus presently contemplated as the best mode of carrying out the invention commercially but not restrictive of the various ways it could be done is shown in the accompanying drawings, in which.

DETAILED DESCRIPTION OF THE ILLUSTRATED EMBODIMENTS

Figures 1, 1A:
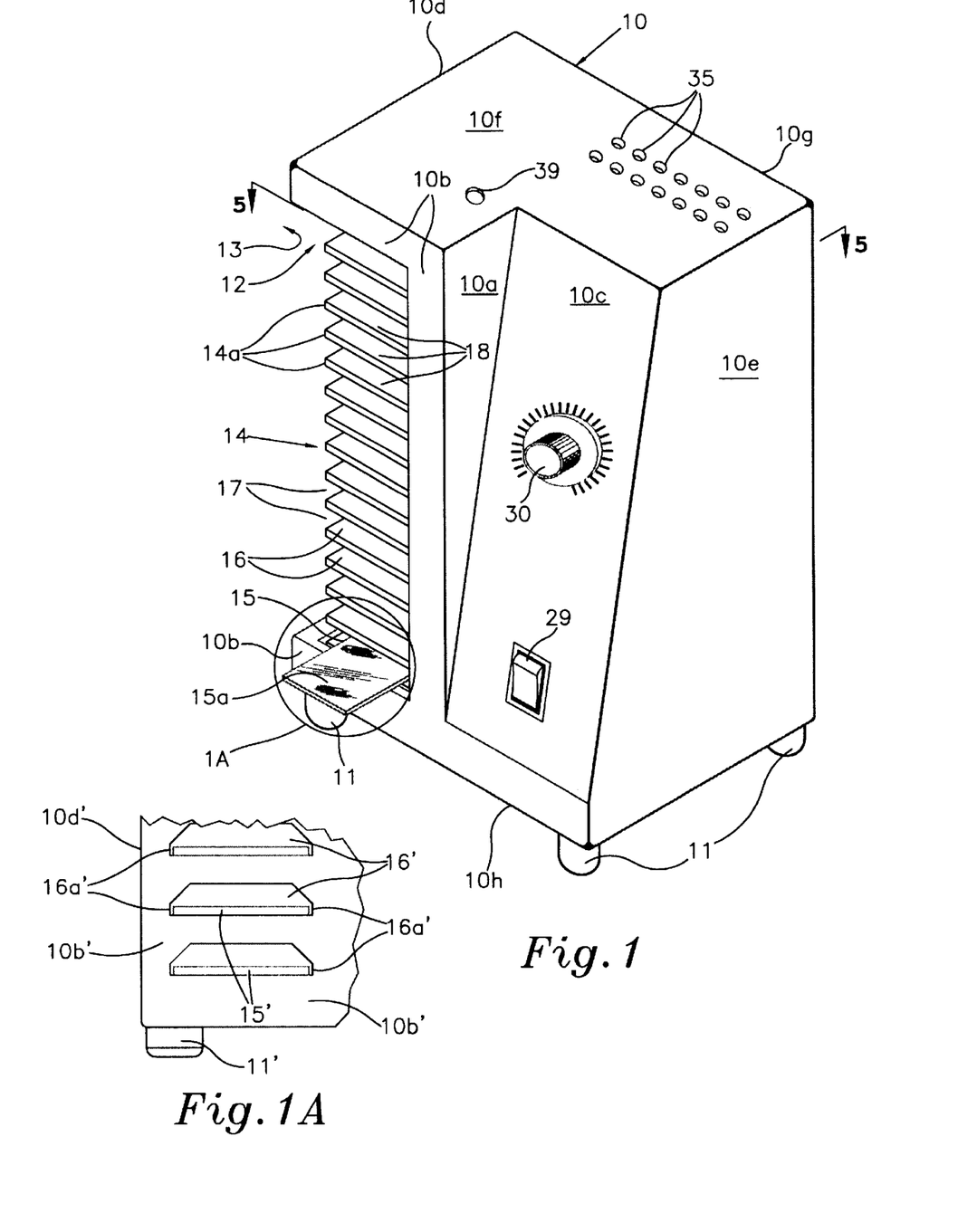
FIG. 1 is a perspective view looking toward the front and one side of a housing, with a microscope slide in place in and protruding from the bottom compartment of a rack structure within the housing.
FIG. 1A, an enlarged view in front elevation of that portion of FIG. 1 encircled by the line 1A and modified in accordance with an alternative construction.

In the form of the invention illustrated in FIG. 1, an upstanding housing 10 serves as at least a partial enclosure for microscope-slide-receiving-and-supporting rack structure and includes a plastic portion that is thermoformed from a flame retardant, thermoplastic material, such as an acrylic polyvinyl chloride, to provide a front wall that is deeply divided, upwardly and downwardly, by a backwardly offset but otherwise vertical, wall part 10*a*. The front of the housing 10 also includes a vertical, corner, front wall part 10*b* and a backwardly sloping, front wall part 10*c*. Such plastic portion of housing 10 also provides vertical side walls 10*d* and 10*e*, respectively, and horizontal top wall 10*f*. A vertical back wall 10*g* and horizontal bottom wall 10*h* are preferably provided by bending an elongate sheet of preferably twelve gauge aluminum and by fastening it to the plastic in any suitable manner, as for example as shown at 10*i* in FIGS. 2, 3, 4, 6, and 7, where screws are used to engage bosses provided by the thermoplastic portion of the housing.

Figure 4:
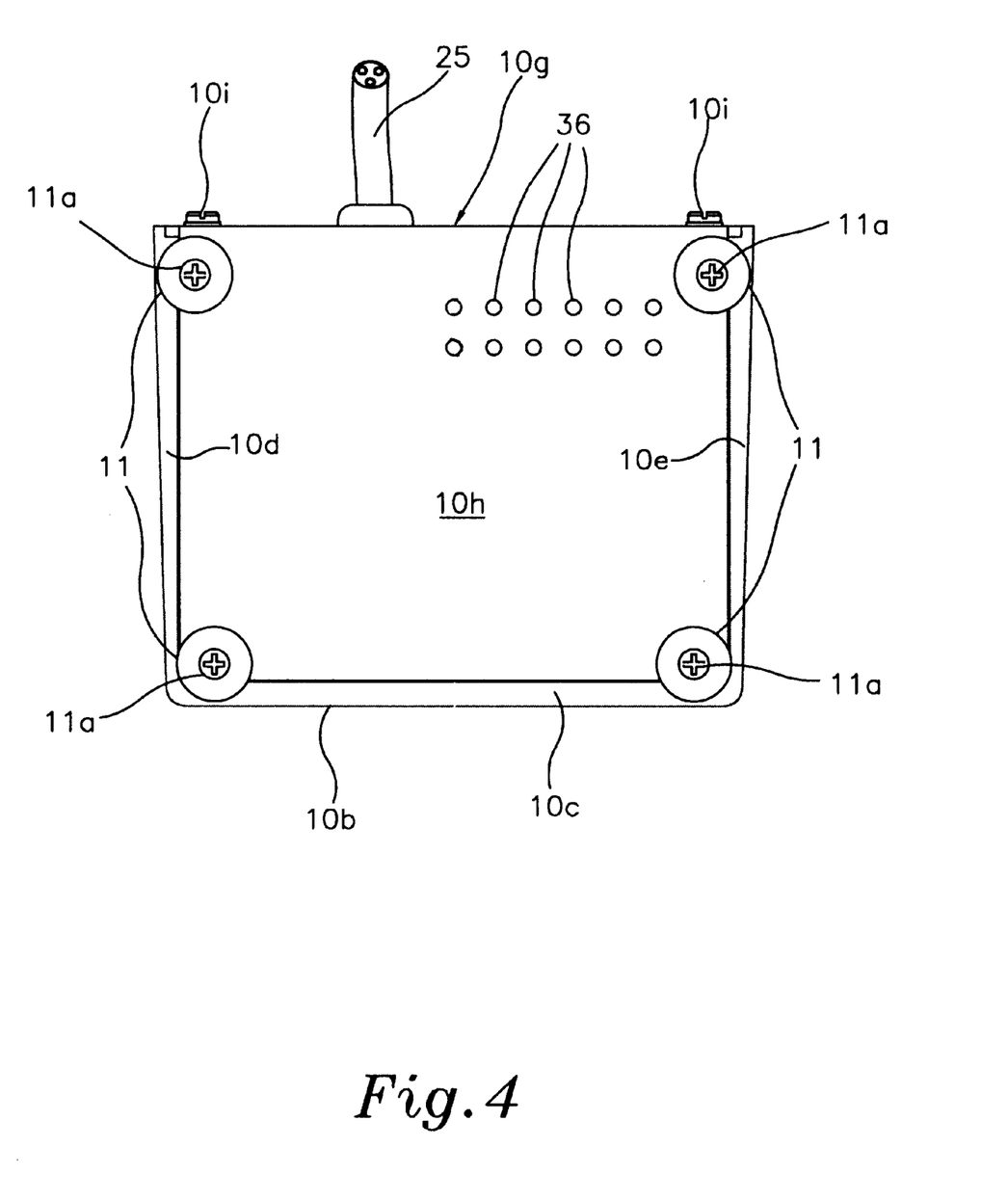
FIG. 4, a corresponding bottom plan view.
Figure 7:
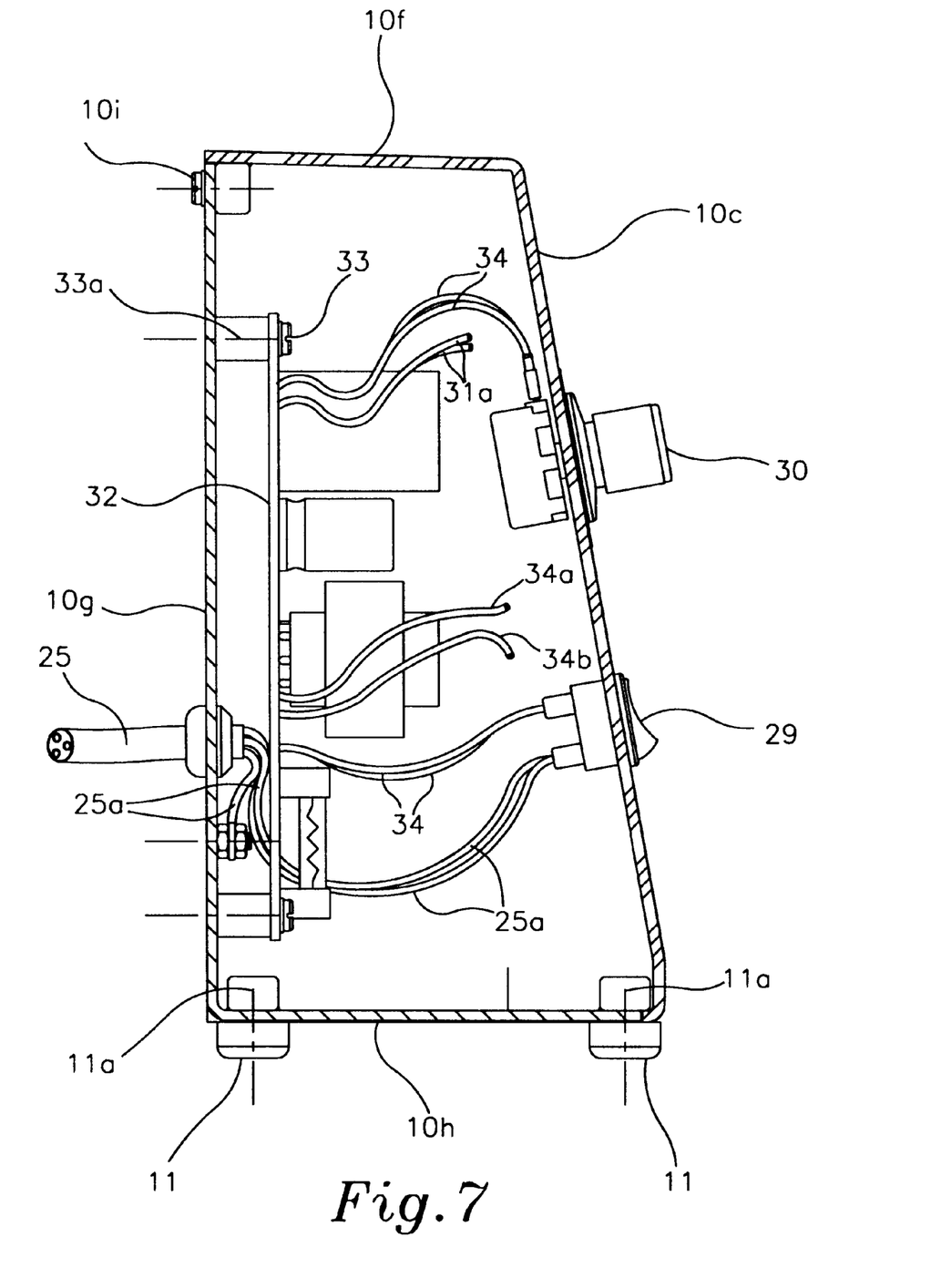
FIG. 7, a view in vertical section taken along the line 7—7 of FIG. 5.

For supporting housing 10 above floor level, four feet 11 are here shown as fastened to the underside of bottom wall 10*h* at the corners thereof, as for example as shown at 11*a* in FIGS. 4 and 7.

Figures 2, 2A:
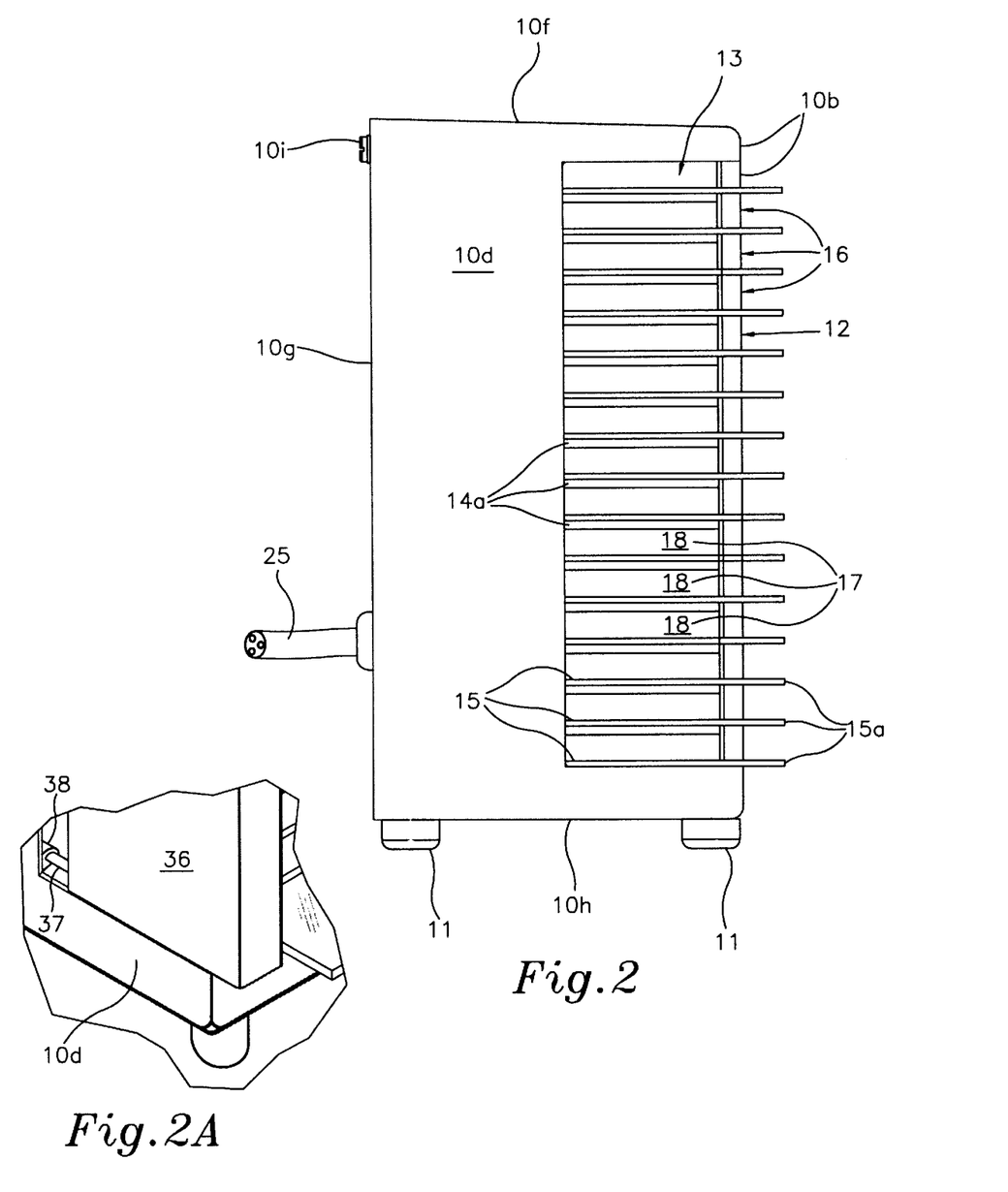
FIG. 2, a view in left-hand side elevation of the embodiment shown in FIG. 1.
FIG. 2A, a fragmentary view showing in perspective a lower forward portion of FIG. 2 with only the lowermost slide in place and showing portions of a removable closure slide for the open side and part of the open portion of the front of the housing of FIGS. 1 and 2.
Figure 3:
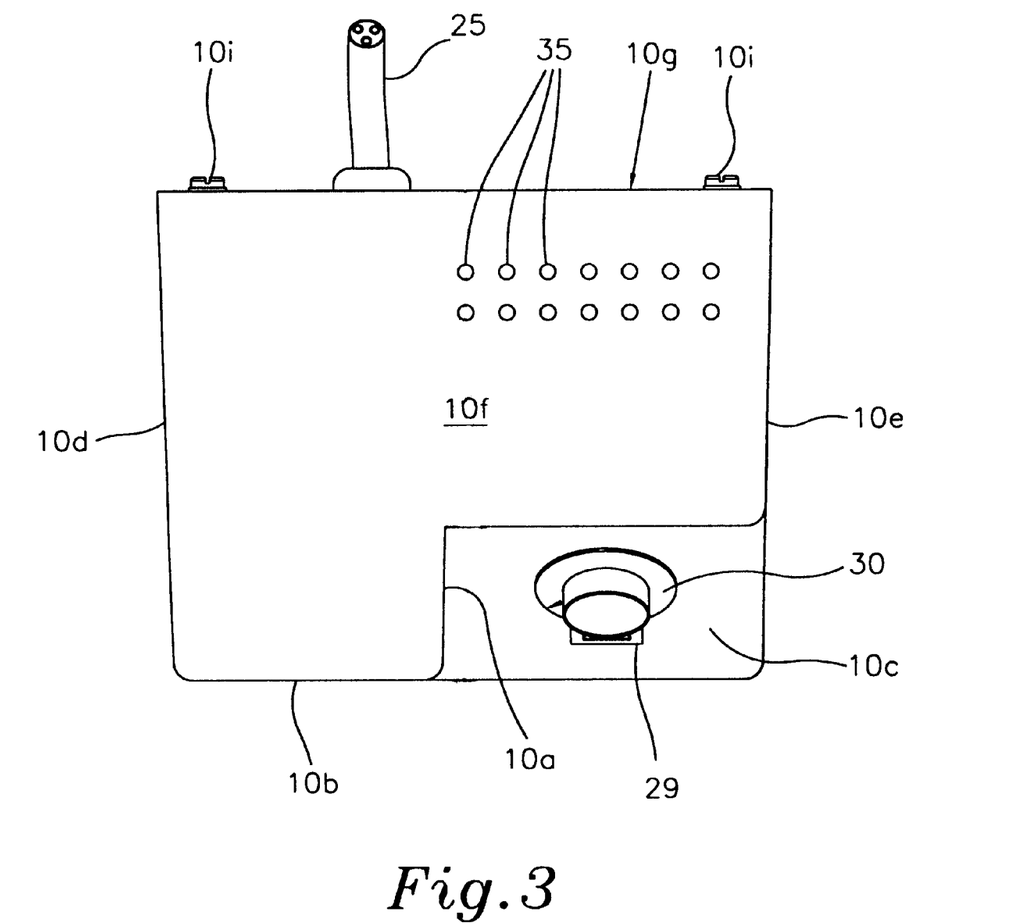
FIG. 3, a top plan view of the embodiment of FIG. 1.
Figure 5:
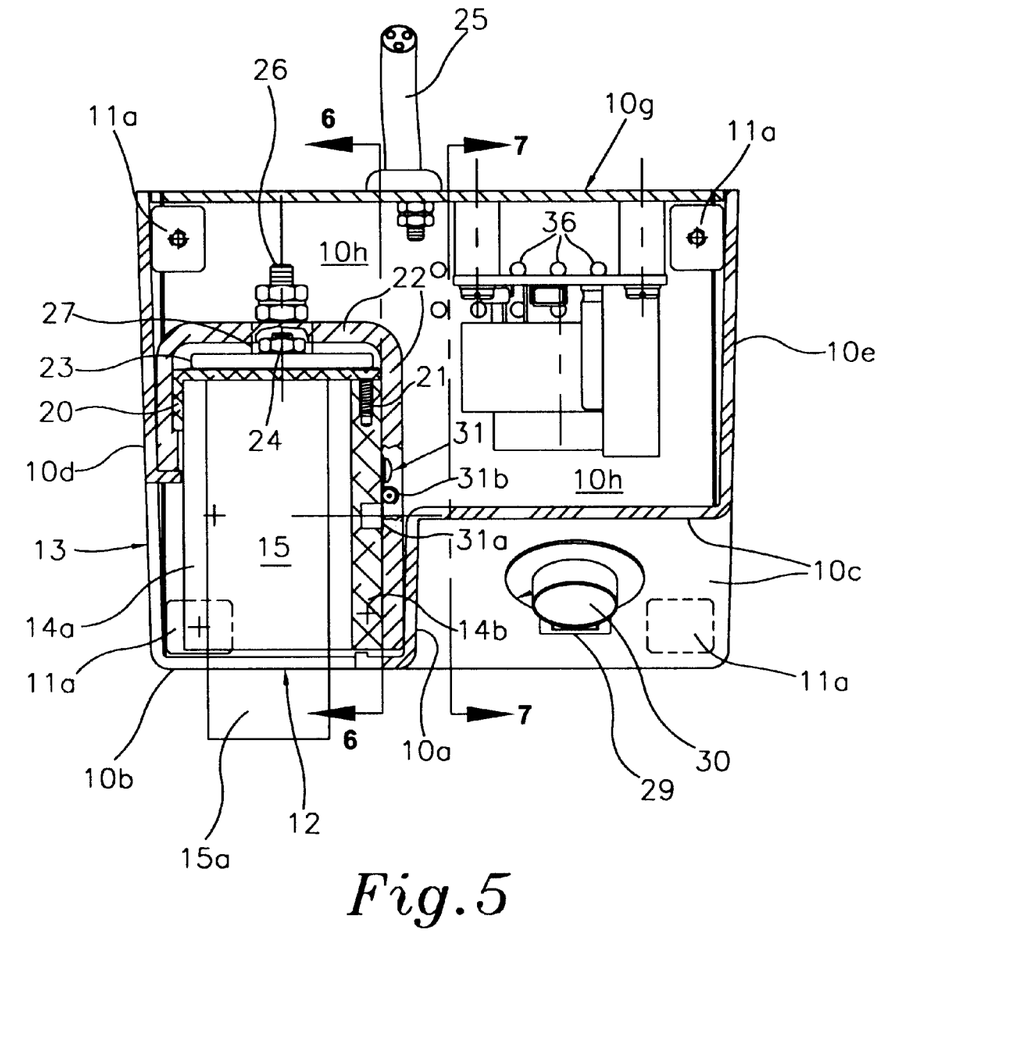
FIG. 5, a view in horizontal section taken along the line 5—5 of FIG. 1.

Front wall portion 10*b* and an adjoining portion of side wall 10*d* are usually left open along much of their heights, as at 12 and 13, respectively, FIGS. 1, 2, and 5, to provide access along the front and a side of a front corner of housing 10 to the interior thereof, in which is mounted a rack structure 14 having an upstanding series of microscope-slide-supporting members, here shown as shelves 14*a*, for receiving a desired number of microscope slides to be heated, see the slide 15 in FIG. 1 and similar slides in FIG. 2. However, those receiving and supporting members need not be shelves so long as they are structurally such as will receive and support at least one microscope slide preferably flatwise. As here shown, there is provision in the rack structure for fifteen slides lying flatwise and singly on the shelves, respectively, see particularly FIGS. 2 and 5, but this is subject to variation depending upon the desired size of housing 10 and on whether two or more slides are to lie side-by-side on a shelf 14*a*.

Rack structure 14 is preferably constructed of heat-conductive material, such as by extruding aluminum (or by die casting, machining, or other well-known technique) to provide the shelves 14a extending integrally from wall 14b thereof, FIG. 5, to form vertical series of slots 16 and 17, respectively, FIGS. 1 and 2, leading into heating compartments 18 for the microscope slides 15, which usually carry specimens (not shown) on their upper receiving faces. A forward end portion 15a of each slide preferably protrudes from the rack structure to remain relatively cool and to facilitate handling.

The front opening 12 and the side opening 13 at an open corner of rack 14 and of housing 10 permit the slides 15 to be inserted into the respective compartments 18, both through the corresponding front slots 16 and side slots 17, FIG. 1, the person loading the slides being able to use a finger or fingers to push along the length of a slide to facilitate its insertion into its corresponding compartment 18.

An optional feature shown in FIG. 1A is to have a full front wall portion 10b', instead of the opening 12, and a full side wall 10d', instead of the opening 13. Microscope-slide-receiving slots 16', diagonally inturned at opposite ends and above the slide-receiving bottoms thereof to overhang tracks 16a' for the narrow longitudinal sides of the slides 15' to prevent inadvertent raising of the slides during insertion and removal thereof and consequent scraping off of specimens carried thereby by contact with the upper defining edges of the slots as could conceivably take place in the embodiment of FIGS. 1–7.

Figure 6:
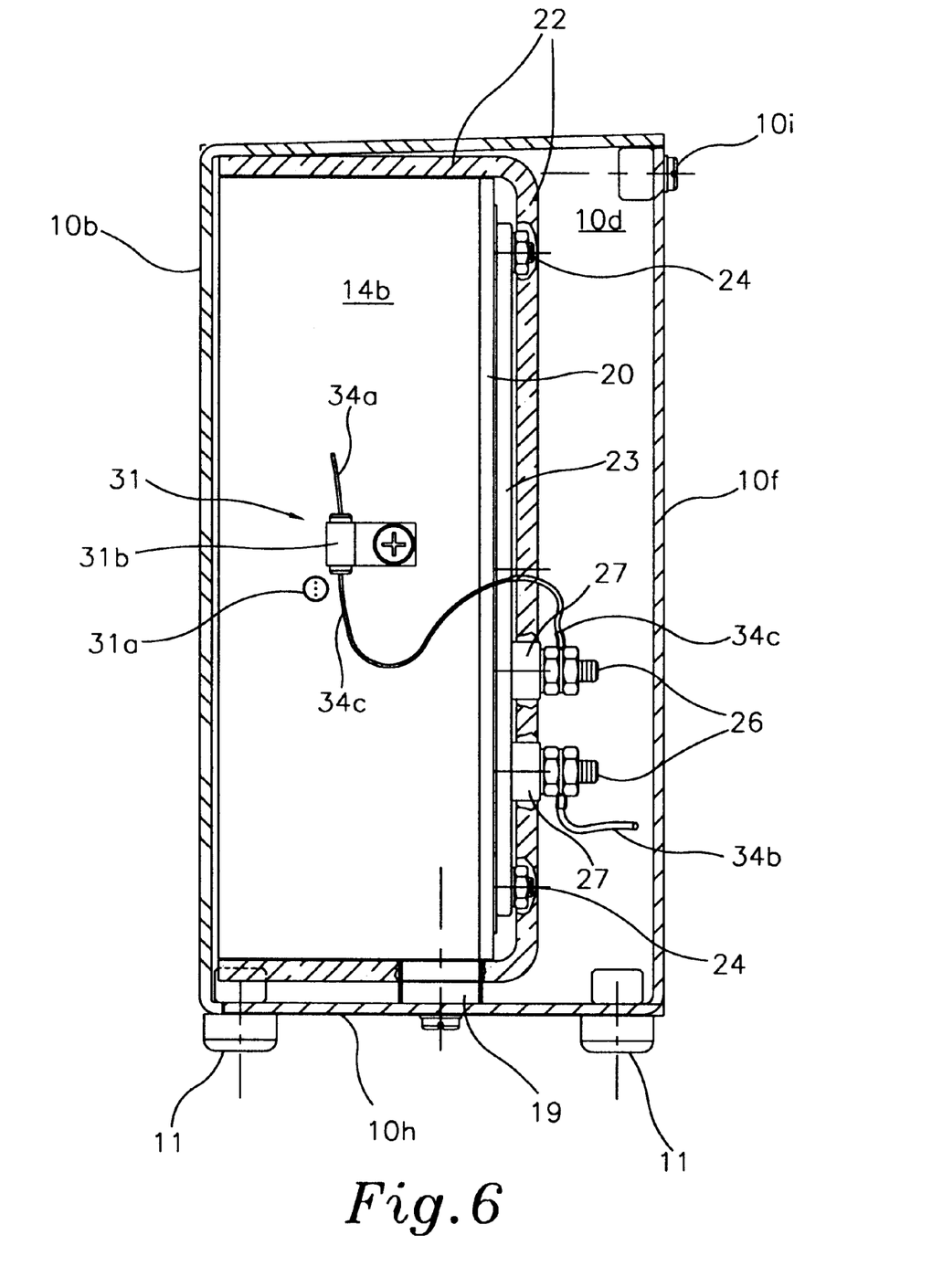
FIG. 6, a view in vertical section taken along the line 6—6 of FIG. 5.

It is usual to mount rack structure 14 above bottom wall 10h of housing 10 by means of brackets 19, FIG. 6, and to provide a separate rack back wall 20, FIG. 5, of L-formation as shown, from aluminum, and to attach it to rack side wall 14b by screws 21, and, further, to cover the rack structure with heat insulation material 22.

For heating the slide-supporting rack members, i.e., the shelves 14a, an elongate, electrically resistive heater plate 23, FIGS. 5 and 6, is, as here shown, fastened to rack back wall 20, as by bolts 24. An AC power cable 25, extending from any suitable power source, supplies electricity to heater plate 23 via wires 25a, FIG. 7, connected to electrical terminals 26, FIG. 6, for the heating plate that pass through blocks 27 in reaching the heater plate. Such cable also supplies electricity to a conventional temperature sensor, proportional comparator control circuit, and solid state relay, all indicated as such in FIG. 8.

A manual on-and-off switch 29, FIGS. 1, 3, 5, and 7, and a manual, temperature-adjusting switch 30 are mounted on front wall part 10c of housing 10. The temperature sensor assembly, designated 31 in FIGS. 5 and 6, is preferably one combining a linear temperature sensor 31a with a thermal fuse 31b and is preferably attached to wall 14b of rack structure 14 in any suitable manner.

Figure 8:
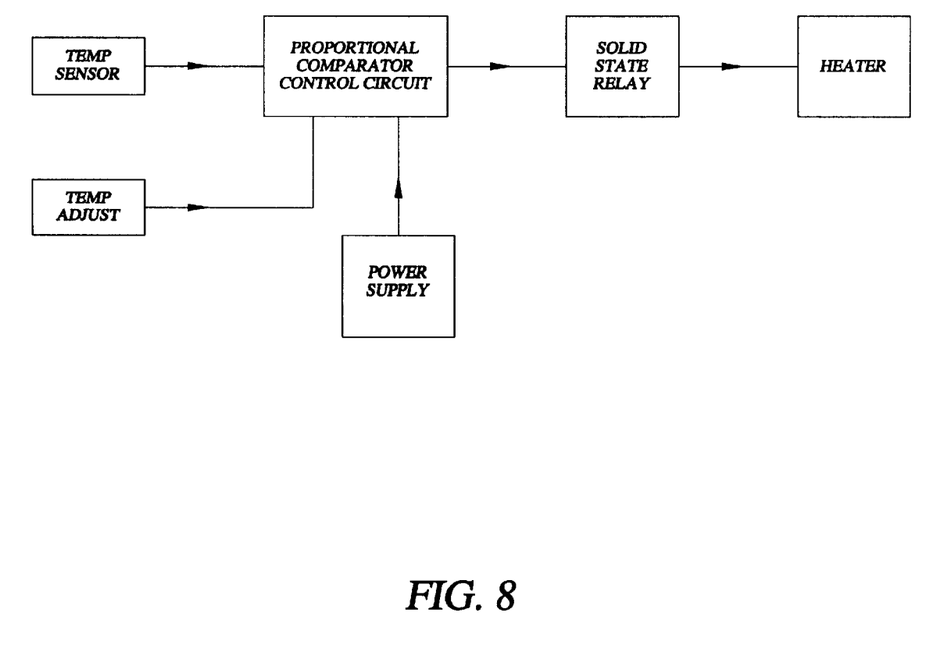
FIG. 8, a block diagram of the electrical system for controlling heating of the slides.

Fastened to back wall 10g of housing 10 on an elongate plate 32, FIG. 7, as by screws 33, passing through blocks of electrical insulation 33a is a thermostat assembly comprising electrical components serviced, along with on-off switch 29 and temperature adjusting switch 30, by electrical wires 34, 34a, and 34b, respectively, bringing power from the power supply of FIG. 8.

As shown in FIG. 4, vent openings 35 in bottom wall 10h and similar vent openings in top wall 10f or elsewhere, as in the upper part of back wall 10g of housing 10, may be provided if found useful in facilitating proper control of heat within the housing.

As indicated by the showing of microscope slide 15 in FIG. 1 and a full showing of such slides in FIG. 2, the shelves 14a may be somewhat shorter than a typical slide to limit the extent of slide insertion and to provide for positioning of a slide by the user so that a grasping portion 15a extends about three-quarters of an inch from the entrance of the slot to remain relatively cool and easily available for grasping.

It is preferred that the temperature range for the shelves and for the compartments be adjustable from about 40° C. to about 100° C., plus or minus about 5% of the selected temperature, depending upon heat take-up capacity of the slides to be used. The time for heating the slides will seldom be less than ten minutes and can be as much as necessary to accomplish the purpose.

While the foregoing use of heated shelves is presently contemplated as the best manner of carrying out the invention commercially, it should be realized that both the shelves and the compartments 18, or either, can be heated in various ways, for example by circulating heated air within the housing and through the compartments; also, doors or other closures for selectively closing one or both of the openings 12 and 13 in housing 10 may be provided if desired. Thus, as shown in FIG. 2A, a closure 36 for side opening 12 and for the adjoining corner portion of front opening 13 of housing 10 in FIGS. 1 and 2, may be provided to slide along the upper edge of the lower forward portion of housing side wall 10d, FIG. 2A, and to push fastening pins 37 (the upper one not being shown) into receiving holes in respective bosses 38, that extend inwardly from such side wall 10d. This closure 36 or other closures, such as doors that are hinged to housing side wall 10d to swing open and closed, may be provided if desired to conserve heat and to be removed or opened during loading and removal of the slides 15 or cleaning of the rack structure.

To check the temperature within housing 10 and rack structure 14 from time to time, an opening, as at 39, FIG. 1, may be provided through housing top wall 10f at a suitable location therein for manual insertion and withdrawal of a thermometer.

While the housing and rack structure have been spoken of and illustrated herein as "upstanding", it should be realized that several sections of relatively short columns of shelves or other microscope-slide-receiving and supporting members may be provided side-by-side in a single facility to handle the required total number of microscope slides, one above another.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. Apparatus for heating multiple, elongate, microscope slides, comprising rack structure having an upstanding series of slide-supporting members spaced apart one above another to provide a substantially corresponding, upstanding series of heating chambers open at at least a set of corresponding ends thereof for the insertion and removal of said microscope slides, the respective heating chambers of said series having an effective slide-receiving length sufficiently short of the length of said microscope slides to receive only so much of the length of a said microscope slide as will leave a relatively short end of a received slide protruding from the open end of the chamber for manual grasping; and structure by which heat can be supplied to the interior of said rack structure.

2. Apparatus according to claim 1, wherein the slide-supporting members comprise an upstanding series of heat-conductive shelves extending transversely to form a corresponding series of heating compartments between said shelves and with microscope-slide-receiving-and-removing slots as the end openings of the heating compartments.

3. Apparatus according to claim 2, wherein the slide-supporting members comprise a series of heat-conductive shelves joined together to provide the rack structure; and the heat-supplying structure comprises a heater attached to said rack structure for heating the series of shelves by conduction of heat.

4. Apparatus according to claim 3, wherein the slide-supporting members are aluminum.

5. Apparatus according to claim 2, wherein the rack structure is mounted in a protective housing having slots confronting the slots of the rack structure, the said confronting slots being defined upwardly by wall portions of said housing which, at the ends of said confronting slots, overhang slide-supporting wall portions of said housing that define the bottoms of said confronting slots, said slots leaving sufficient space above received slides to prevent scraping of carried materials therefrom, and the overhanging wall portions preventing any excess raising of the slides during insertion and removal thereof.

6. Apparatus according to claim 2, wherein the rack structure is mounted in a protective housing and is constructed of heat-conductive material, the said housing being of rectangular, substantially box formation and being partially molded from flame-retardant, plastic material.

7. Apparatus for heating multiple, elongate, microscope slides, comprising rack structure having an upstanding series of slide-supporting members spaced apart one above another to provide a substantially corresponding, upstanding series of heating chambers open at at least a set of corresponding ends thereof for the insertion and removal of said microscope slides, the said chambers of said rack structure being open laterally from the open ends thereof at a corner of said rack structure to provide a slide-receiving corner for said rack structure wherein the said end openings and the said lateral openings of the respective chambers confront each other at said corner along a significant part of the length of the microscope slide being introduced into the chamber so as to facilitate introduction of the slide into the chamber; and structure by which heat can be supplied to the interior of said rack structure.

8. Apparatus according to claim 7, wherein the slide-supporting members comprise a series of heat-conductive shelves forming the heating chambers therebetween; heat-conductive plates substantially surrounding portions of said chambers that are not open but are in heat-conductive contact with said shelves; and the structure for supplying heat comprises a heater plate in heat-conductive contact with said heat-conductive plates.

9. Apparatus according to claim 1, wherein the rack structure is mounted in a protective housing along with heat control instrumentation.

10. Apparatus according to claim 9, wherein the protective housing has walls molded from a flame-retardant, thermoplastic material and at least one wall of heat-conductive material on which is mounted the heat control instrumentation.

11. Apparatus according to claim 9, wherein the heat control instrumentation comprises temperature sensor, proportional comparative control circuitry, and solid state relays in said control circuitry.

12. A method of heating multiple, elongate, microscope slides within heating apparatus which includes a receiving and supporting rack structure having multiple, open-ended, slide-receiving and slide-supporting, heating chambers, comprising inserting the slides in said chambers so that an end portion of the received slide projects from and exteriorly of the chamber in which it is heated, sufficiently to permit comfortable manual grasping in the removal of the heated slide from said apparatus.

\* \* \* \* \*